US007999100B2

(12) United States Patent
Learmonth et al.

(10) Patent No.: US 7,999,100 B2
(45) Date of Patent: Aug. 16, 2011

(54) METHOD FOR CHIRAL INVERSION OF (S)-(+)-AND (R)-(−)-10,11-DIHYDRO-10-HYDROXY-5H-DIBENZ/B,F/AZEPINE-5-CARBOXAMIDE AND OPTICALLY ENRICHED MIXTURES THEREOF

(75) Inventors: David Alexander Learmonth, Alfena (PT); Günter Weingaertner, Dottikon (CH); Matthias Kraemer, Mellingen (CH)

(73) Assignee: Bial-Portela CA & S.A., S. Mamede do Coronado (PT)

( * ) Notice: Subject to any disclaimer, the term of this patent is extended or adjusted under 35 U.S.C. 154(b) by 844 days.

(21) Appl. No.: 11/572,077

(22) PCT Filed: Jul. 13, 2005

(86) PCT No.: PCT/GB2005/002744
§ 371 (c)(1),
(2), (4) Date: Jan. 28, 2008

(87) PCT Pub. No.: WO2006/005951
PCT Pub. Date: Jan. 19, 2006

(65) Prior Publication Data
US 2008/0293934 A1 Nov. 27, 2008

(30) Foreign Application Priority Data

Jul. 13, 2004 (GB) .................... 0415664.2

(51) Int. Cl.
*C07D 223/22* (2006.01)
*C07D 401/12* (2006.01)
(52) U.S. Cl. ...................................... 540/589
(58) Field of Classification Search .................. 540/589
See application file for complete search history.

(56) References Cited

U.S. PATENT DOCUMENTS
5,753,646 A 5/1998 Benes et al.

FOREIGN PATENT DOCUMENTS
WO 02/092572 A1 11/2002

OTHER PUBLICATIONS

Benes, Jan, et al., "Anticonvulsant and Sodium Channel-Blocking Properties of Novel 10,11-Dihydro-5H-dibenz[b,f] azepine-5-carboxamide Derivatives," Journal of Medicinal Chemistry, 1999, pp. 2582-2587, vol. 42, No. 14, American Chemical Society.
Cid, José, et al., "Synthesis and structure-activity relationship of 2-(aminoalkyl)-3,3a,8,12b-tetrahydro-2H-dibenzocyclohepta[1,2-b]furan derivatives: a novel series of 5-HT2A/2C receptor antagonists," Bioorganic & Medicinal Chemistry Letters, 2004, pp. 2765-2771, vol. 14, Elsevier Ltd.
Mitsunobu, Oyo, "The Use of Diethyl Azodicarboxylate and Triphenylphosphine in Synthesis and Transformation of Natural Products," Synthesis, Jan. 1981, pp. 1-28, Georg Thieme Verlag, Stuttgart-New York.
Schütz, H., et al., "The metabolism of 14C-oxcarbazepine in man," Xenobiotica, 1986, pp. 769-778, vol. 16, No. 8.
Foreign communication from a related counterpart application—International Search Report, PCT/GB2005/002744, Oct. 20, 2005, 2 pgs.
Foreign communication from a related counterpart application—International Preliminary Report on Patentability, PCT/GB2005/002744, Jan. 16, 2007, 7 pgs.

*Primary Examiner* — Brenda Coleman
(74) *Attorney, Agent, or Firm* — Conley Rose, P.C.; Rodney B. Carroll

(57) ABSTRACT

A method for chiral inversion of optically pure or optically enriched mixtures of (S)-(+)-10,11-dihydro-10-hydroxy-5H-dibenz/b,f/azepine-5-carboxamide (I) and (R)-(−)-10,11-dihydro-10-hydroxy-5H-dibenz/b,f/azepine-5-carboxamide (II).

28 Claims, No Drawings

METHOD FOR CHIRAL INVERSION OF (S)-(+)-AND (R)-(−)-10,11-DIHYDRO-10-HYDROXY-5H-DIBENZ/B,F/AZEPINE-5-CARBOXAMIDE AND OPTICALLY ENRICHED MIXTURES THEREOF

CROSS-REFERENCE TO RELATED APPLICATIONS

This application is a filing under 35 U.S.C. 371 of International Application No. PCT/GB2005/002744 filed Jul. 13, 2005, entitled "Method for chiral inversion of (S)-(+)- and (R)-(−)-10,11-dihydro-10-hydroxy-5H-dibenz/b,f/azepine-5-carboxamide and optically enriched mixtures thereof," claiming priority of Great Britain Patent Application No. GB 0415664.2 filed Jul. 13, 2004, which applications are incorporated by reference herein in their entirety.

FIELD OF THE INVENTION

This invention relates to a method for chiral inversion of optically pure or optically enriched mixtures of (S)-(+)-10, 11-dihydro-10-hydroxy-5H-dibenz/b,f/azepine-5-carboxamide and (R)-(−)-10,11-dihydro-10-hydroxy-5H-dibenz/b,f/azepine-5-carboxamide (compounds of formulas (I) and (II) respectively).

BACKGROUND OF THE INVENTION

Racemic (±)-10,11-dihydro-10-hydroxy-5H-dibenz/b,f/azepine-5-carboxamide (III) has been shown to possess anticonvulsant activity (Schutz, H. et al., Xenobiotica, 16, 769-778 (1986)), and is the principal metabolite of the established anti-epileptic drug oxcarbazepine (IV). This racemate (III) serves as a useful intermediate for the preparation of optically pure (S)-(−)-10-acetoxy-10,11-dihydro-5H-dibenz/b,f/azepine-5-carboxamide (V) and (R)-(+)-10-acetoxy-10,11-dihydro-5H-dibenz/b,f/azepine-5-carboxamide (formula VI), two more recently disclosed, single-enantiomer putative anti-epileptic drugs demonstrating improved biological properties (Benes, J. et al., J. Med. Chem., 42, 2582-2587 (1999)). The (S)-(−)-enantiomer (V) in particular has been shown to display a very favourable anti-convulsant profile.

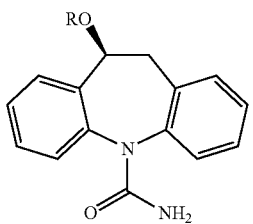

(I), R = H
(V), R = COCH₃

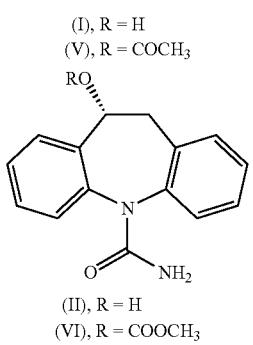

(II), R = H
(VI), R = COOCH₃

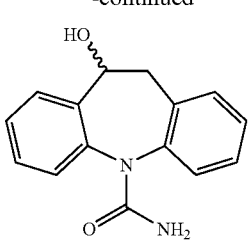

(III)

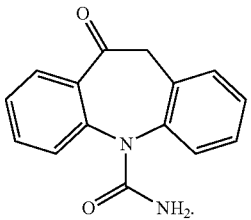

(IV)

A key step in the synthesis of either of the optically pure individual acetate esters (V) or (VI) involves the resolution of racemic (±)-10,11-dihydro-10-hydroxy-5H-dibenz/b,f/azepine-5-carboxamide (III) into its individual, optically pure stereoisomers, (S)-(+)-10,11-dihydro-10-hydroxy-5H-dibenz/b,f/azepine-5-carboxamide (I) and (R)-(−)-10,11-dihydro-10-hydroxy-5H-dibenz/b,f/azepine-5-carboxamide (II), which are the principal intermediates for synthesis of the enantiomerically pure acetates (V) and (VI). An improved method for this resolution was recently disclosed involving the efficient separation of diastereoisomeric tartrate half-esters of racemic (±)-10,11-dihydro-10-hydroxy-5H-dibenz/b, f/azepine-5-carboxamide (III) (Learmonth, D., PCT/GB02/02176).

Racemic (±)-10,11-dihydro-10-hydroxy-5H-dibenz/b,f/azepine-5-carboxamide (III) can be easily prepared by reduction of the ketone group of oxcarbazepine (IV), by the use of, for example, metal hydrides in alcoholic medium. However, oxcarbazepine (IV) is an expensive substance, and despite the very efficient resolution procedure (around 98% yield based on a single diastereoisomer), development of say only the (S)-(−)-acetate (V) would mean the loss of approximately 50% of costly material. It would thus be highly desirable to have a method of recycling this unwanted, but expensive (R)-(−)-10,11-dihydro-10-hydroxy-5H-dibenz/b,f/azepine-5-carboxamide (II) which can be recovered from the resolution mixture. However recycling of this material is very complicated due to the propensity for elimination of water across the C10-C11 junction even under very mild conditions, which provides an olefinic product of negligible economic interest. Notwithstanding, recycling could be envisaged to involve inversion of the chiral centre at C-10 by a Mitsunobu reaction protocol with concomitant esterification (Mitsunobu, O., Synthesis, 1-29, (1981)), whereby the recovered but unwanted optically enriched (R)-(−)-10,11-dihydro-10-hydroxy-5H-dibenz/b,f/azepine-5-carboxamide (II) is converted directly to the (S)-(−)-acetate (V) or to analogous chirally inverted ester derivatives of potential biological interest. The Mitsunobu procedure should preferably involve the use of readily available solvents and reagents, and be operationally simple whilst affording good yields of chirally-inverted, esterified products. Additionally, it would be highly desirable for large-scale manufacturing purposes to develop the Mitsunobu inversion reaction so as to obtain the desired inverted products in high purity and yield through a significantly simplified purification process without resort to inconvenient and tedious purification by column chromatography over silica gel which is usually required to remove unwanted reagents and by-products associated with the Mitsunobu reaction, such as, for example, triphenylphosphine, triphenylphosphine oxide, disubstituted azodicarboxylate and reduced hydrazine-derivatives thereof.

SUMMARY OF THE INVENTION

It has now been found that the reaction of optically enriched (enantiomeric excesses in the range from 1 to 99.5%) (R)-(−)-10,11-dihydro-10-hydroxy-5H-dibenz/b,f/azepine-5-carboxamide (II) or (S)-(+)-10,11-dihydro-10-hydroxy-5H-dibenz/b,f/azepine-5-carboxamide (I) with a combination of a tri-substituted phosphine, a disubstituted azodicarboxylate and a carboxylic acid nucleophile in a suitably inert solvent gives good yields of chirally inverted esterified products, without significant formation of undesired olefinic products, which can be surprisingly easily separated from the further unwanted Mitsunobu reaction by-products by crystallisation from a suitable solvent without the need for chromatographic separation, giving the method of the present invention according to the following synthetic scheme:

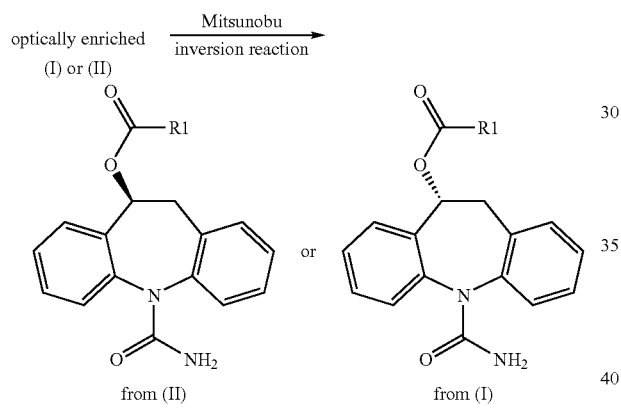

DETAILED DESCRIPTION OF THE INVENTION

According to the present invention, the C-10 chiral alcohol functionality of optically pure or optically-enriched (R)-(−)-10,11-dihydro-10-hydroxy-5H-dibenz/b,f/azepine-5-carboxamide (II) or (S)-(+)-10,11-dihydro-10-hydroxy-5H-dibenz/b,f/azepine-5-carboxamide (I) undergoes a chiral switch and concomitant esterification via a Mitsunobu reaction with suitable carboxylic acid nucleophiles, such as, for example, aliphatic, cyclic, aromatic or heteroaromatic carboxylic acids including formic acid, acetic acid, propionic acid, butyric acid, cyclohexanoic acid, optionally substituted benzoic acids, nicotinic acid and the like. The carboxylic acid nucleophile can be used in a 1.02-5 molar ratio with respect to the optically pure or enriched alcohol (I) or (II), but preferably in the range 1.05-2.2. The reaction is carried out using a redox combination of a tri-substituted phosphine and disubstituted azodicarboxylate. Typical phosphines which are useful in the reaction include tri-n-propylphosphine, tri-n-butylphosphine, triphenylphosphine, tri-o-tolylphosphine, diphenyl(2-pyridyl)phosphine, (4-dimethylamino)diphenylphosphine, tris(dimethylamino)phosphine and the like. If preferred, the tri-substituted phosphine can be supported on an inert polymer. Preferred disubstituted azodicarboxylates include dimethylazodicarboxylate, diethylazodicarboxylate, diisopropylazodicarboxylate, di-tert-butylazodicarboxylate, 1,1'-(azodicarbonyl)dipiperidine and the like. Preferably, the tri-substituted phosphine and disubstituted azodicarboxylate are both used in equimolar quantities with respect to the optically pure or enriched alcohol (I) or (II). The reaction can be run in a solvent which is inert under the reaction conditions, such as, for example, chlorinated solvents including dichloromethane, chloroform and carbon tetrachloride, aliphatic or cyclic ethers including diethyl ether, tetrahydrofuran and dioxane, amides including dimethylformamide and hydrocarbons including toluene and the like. The reaction can be carried out over a wide range of temperatures, from −78° C. to the boiling point of the solvent used, but preferably in the range 0° C.-30° C. The inverted products can be very easily isolated from the reaction mixture by evaporation of the reaction solvent, and replacement with a suitable crystallisation solvent such as for example, lower aliphatic alcohols such as methanol, ethanol or isopropanol, with or without addition of water, esters including ethyl acetate and isopropyl acetate or ketones including acetone and methyl ethyl ketone. The inverted product is then recovered by filtration and, if preferred, can be further purified by slurrying or recrystallisation from suitable solvents, such as, for example, lower aliphatic alcohols such as methanol, ethanol or isopropanol, with or without addition of water, esters including ethyl acetate or isopropyl acetate or ketones including acetone and methyl ethyl ketone. The optical purity of the inverted, esterified product can be easily determined by chiral HPLC analysis.

According to another aspect of the invention, there is provided a method for the preparation of a compound of the general formula (VIII):

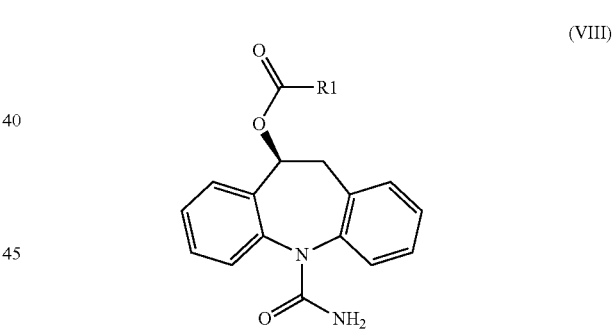

where $R_1$ is hydrogen, alkyl, halogenalkyl, aralkyl, cycloalkyl, cycloalkylalkyl, aryl or pyridyl; the term alkyl means a straight or branched hydrocarbon chain containing from 1 to 18 carbon atoms, preferably 1 to 8 carbon atoms, more preferably 1 to 4 carbon atoms; the term halogen means fluorine, chlorine, bromine or iodine; the term cycloalkyl means an alicyclic saturated group with 3 to 6 carbon atoms, preferably 5 or 6 carbon atoms; and the term aryl means an unsubstituted phenyl group or phenyl substituted by alkoxy, halogen or nitro group, said method comprising reacting optically pure or optically enriched (R)-(−)-10,11-dihydro-10-hydroxy-5H-dibenz/b,f/azepine-5-carboxamide (II) with the corresponding carboxylic acid nucleophile by a process as described above.

According to another aspect of the invention, there is provided a method for the preparation of a compound of the general formula (IX):

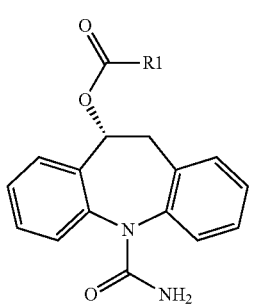

(IX)

where $R_1$ is hydrogen, alkyl, halogenalkyl, aralkyl, cycloalkyl, cycloalkylalkyl, aryl or pyridyl; the term alkyl means a straight or branched hydrocarbon chain containing from 1 to 18 carbon atoms, preferably 1 to 8 carbon atoms, more preferably 1 to 4 carbon atoms; the term halogen means fluorine, chlorine, bromine or iodine; the term cycloalkyl means an alicyclic saturated group with 3 to 6 carbon atoms, preferably 5 or 6 carbon atoms; and the term aryl means an unsubstituted phenyl group or phenyl substituted by alkoxy, halogen or nitro group, said method comprising reacting optically enriched (S)-(+)-10,11-dihydro-10-hydroxy-5H-dibenz/b,f/azepine-5-carboxamide (II) with the corresponding carboxylic acid nucleophile by a process as described above.

Resolution of the racemic (±)-10,11-dihydro-10-hydroxy-5H-dibenz/b,f/azepine-5-carboxamide (III) into its optically pure stereoisomers (S)-(+)-10,11-dihydro-10-hydroxy-5H-dibenz/b,f/azepine-5-carboxamide (I) and (R)-(−)-10,11-dihydro-10-hydroxy-5H-dibenz/b,f/azepine-5-carboxamide (II) is possible as described in more detail in our application no. PCT/GB02/02176. The compounds of formulas (VIII) and (IX) are described in more detail in our U.S. Pat. No. 5,753,646, the contents of which are incorporated herein by reference.

For example, under the present invention, it is now possible to produce (S)-(−)-10-acetoxy-10,11-dihydro-5H-dibenz/b,f/azepine-5-carboxamide (I) directly from (R)-(−)-10,11-dihydro-10-hydroxy-5H-dibenz/b,f/azepine-5-carboxamide (II) of opposite stereochemical configuration, by chiral inversion and concomitant O-acetylation by reaction with acetic acid as nucleophile in the presence of diisopropylazodicarboxylate and triphenylphosphine in a solvent such as tetrahydrofuran.

The compounds described in examples 4 to 23 of U.S. Pat. No. 5,753,646 can be produced by chiral inversion and concomitant esterification using the appropriate carboxylic acid nucleophile. Using the present invention, it is therefore possible to produce all of the following compounds:

(1) 10-acetoxy-10,11-dihydro-5H-dibenz/b,f/azepine-5-carboxamide
(2) 10-benzoyloxy-10,11-dihydro-5H-dibenz/b,f/azepine-5-carboxamide
(3) 10-(4-methoxybenzoyloxy)-10,11-dihydro-5H-dibenz/b,f/azepine-5-carboxamide
(4) 10-(3-methoxybenzoyloxy)-10,11-dihydro-5H-dibenz/b,f/azepine-5-carboxamide
(5) 10-(2-methoxybenzoloxy)-10,11-dihydro-5H-dibenz/b,f/azepine-5-carboxamide
(6) 10-(4-nitrobenzoyloxy)-10,11-dihydro-5H-dibenz/b,f/azepine-5-carboxamide
(7) 10-(3-nitrobenzoyloxy)-10,11-dihydro-5H-dibenz/b,f/azepine-5-carboxamide
(8) 10-(2-nitrobenzoyloxy)-10,11-dihydro-5H-dibenz/b,f/azepine-5-carboxamide
(9) 10-(4-chlorobenzoyloxy)-10,11-dihydro-5H-dibenz/b,f/azepine-5-carboxamide
(10) 10-(3-chlorobenzoyloxy)-10,11-dihydro-5H-dibenz/b,f/azepine-5-carboxamide
(11) 10-(2-acetoxybenzoyloxy)-10,11-dihydro-5H-dibenz/b,f/azepine-5-carboxamide
(12) 10-propionyloxy-10,11-dihydro-5H-dibenz/b,f/azepine-5-carboxamide
(13) 10-butyroyloxy-10,11-dihydro-5H-dibenz/b,f/azepine-5-carboxamide
(14) 10-pivaloyloxy-10,11-dihydro-5H-dibenz/b,f/azepine-5-carboxamide
(15) 10-[(2-propyl)pentanoyloxy]-10,11-dihydro-5H-dibenz/b,f/azepine-5-carboxamide
(16) 10-[(2-ethyl)hexanoyloxy]-10,11-dihydro-5H-dibenz/b,f/azepine-5-carboxamide
(17) 10-stearoyloxy-10,11-dihydro-5H-dibenz/b,f/azepine-5-carboxamide
(18) 10-cyclopentanoyloxy-10,11-dihydro-5H-dibenz/b,f/azepine-5-carboxamide
(19) 10-cyclohexanoyloxy-10,11-dihydro-5H-dibenz/b,f/azepine-5-carboxamide
(20) 10-phenylacetoxy-10,11-dihydro-5H-bibenz/b,f/azepine-5-carboxamide
(21) 10-(4-methoxyphenyl)acetoxy-10,11-dihydro-5H-dibenz/b,f/-azepine-5-carboxamide
(22) 10-(3-methoxyphenyl)acetoxy-10,11-dihydro-5H-dibenz/b,f/azepine-5-carboxamide
(23) 10-(4-nitrophenyl)acetoxy-10,11-dihydro-5H-dibenz/b,f/azepine-5-carboxamide
(24) 10-(3-nitrophenyl)acetoxy-10,11-dihydro-5H-dibenz/b,f/azepine-5-carboxamide
(25) 10-nicotinoyloxy-10,11-dihydro-5H-dibenz/b,f/azepine-5-carboxamide
(26) 10-isonicotinoyloxy-10,11-dihydro-5H-dibenz/b,f/azepine-5-carboxamide
(27) 10-formyloxy-10,11-dihydro-5H-dibenz/b,f/azepine-5-carboxamide
(28) 10-chloroacetoxy-10,11-dihydro-5H-dibenz/b,f/azepine-5-carboxamide
(29) 10-bromoacetoxy-10,11-dihydro-5H-dibenz/b,f/azepine-5-carboxamide
(30) 10-(2-chloropropionyloxy)-10,11-dihydro-5H-dibenz/b,f/azepine-5-carboxamide As already mentioned, optically pure or optically-enriched mixtures of both (R)-(−)- and (S)-(+)-10,11-dihydro-10-hydroxy-5H-dibenz/b,f/azepine-5-carboxamide (III) can be inverted and esterified by the present invention, whereby the desired (R)-(+)- or (S)-(−)-stereoisomers of all of the above compounds may be produced.

These compounds, or pharmaceutically acceptable derivatives thereof (such as salts), can be used in the preparation of pharmaceutical compositions comprising the compound itself, or the derivative, in combination with a pharmaceutically acceptable carrier. Such compositions have anticonvulsant properties and can be used in the treatment of some central and peripheral nervous system disorders, such as epilepsy.

EXAMPLES

The invention disclosed herein is exemplified by the following examples of preparation. It is to be understood that the invention is not to be limited to the exact details of operation, as obvious modifications and equivalents will be apparent to those skilled in the art.

Example 1

Example 1. (S)-(−)-10-Acetoxy-10,11-dihydro-5H-dibenz/b,f/azepine-5-carboxamide (V)

To a stirred suspension of (R)-(−)-10,11-dihydro-10-hydroxy-5H-dibenz/b,f/azepine-5-carboxamide (II) (1.0 g, 3.94 mmol) (98.85% optical purity by chiral HPLC analysis), triphenylphosphine (1.03 g, 3.94 mmol) and acetic acid (0.47 g, 7.88 mmol) in tetrahydrofuran (12 mL) cooled in an ice-water bath was added diisopropylazodicarboxylate (0.80 g, 3.94 mmol) dropwise. After addition was complete, the reaction mixture, which became a cloudy yellow solution, was allowed to stir at room temperature for four hours, whereupon the tetrahydrofuran was evaporated (40° C., water-aspirator pressure). Isopropanol (5 mL) was added to the oily residue and the mixture was warmed to the boiling point of the solvent. The mixture was then allowed to cool to room temperature, and then stored at 5° C. for one hour. The precipitate was collected by filtration, and then recrystallised from isopropanol (4 mL). The crystals were collected by filtration and after drying to constant weight, there was obtained (S)-(−)-10-acetoxy-10,11-dihydro-5H-dibenz/b,f/azepine-5-carboxamide (V) as white crystals (0.48 g, 41%) of m.p. 186-187° C.

Chiral HPLC analysis of this product (LiChroCART 250-4 HPLC Cartridge ChiraDex 5 μm, (Merck), Flowrate: 0.8 mL/min, Mobile Phase: 0.1M $Na_2HPO_4$ buffer pH7/methanol 88:12, sample injected was 20 μL of 0.2 mg analyte/mL dissolved in the mobile phase, and UV detection at 210/254 nm showed complete inversion and O-acetylation with 0.9% (R)-(+)-10-acetoxy-10,11-dihydro-5H-dibenz/b,f/azepine-5-carboxamide (Vi) with retention time 15.98 minutes and 99.2% (S)-(−)-10-acetoxy-10,11-dihydro-5H-dibenz/b,f/azepine-5-carboxamide (V) with retention time of 21.33 minutes.

Example 2

Example 2. (S)-(−)-10-Butyroyloxy-10,11-dihydro-5H-dibenz/b,f/azepine-5-carboxamide To a stirred suspension of (R)-(−)-10,11-dihydro-10-hydroxy-5H-dibenz/b,f/azepine-5-carboxamide (II) (1.0 g, 3.94 mmol) (98.85% optical purity by chiral HPLC analysis), triphenylphosphine (1.03 g, 3.94 mmol) and butyric acid (0.69 g, 7.88 mmol) in tetrahydrofuran (12 mL) cooled in an ice-water bath was added diisopropylazodicarboxylate (0.80 g, 3.94 mmol) dropwise. After addition was complete, the reaction mixture, which became a yellow solution, was allowed to stir at room temperature for two hours, whereupon the tetrahydrofuran was evaporated (40° C., water-aspirator pressure). Isopropanol (5 mL) was added to the oily residue and the mixture was warmed to the boiling point of the solvent. The mixture was then allowed to cool to room temperature, and then stored at 5° C. for one hour. The precipitate was collected by filtration, and then recrystallised from isopropanol (4 mL). The crystals were collected by filtration and after drying to constant weight, there was obtained (S)-(−)-10-butyroyloxy-10,11-dihydro-5H-dibenz/b,f/azepine-5-carboxamide as white crystals (0.57 g, 45%) of m.p. 173-175° C.

Chiral HPLC analysis of this product (LiChroCART 250-4 HPLC Cartridge ChiraDex 5 μm, (Merck), Flowrate: 0.8 mL/min, Mobile Phase: 0.1M $Na_2HPO_4$ buffer pH7/methanol 88:12, sample injected was 20 μL of 0.2 mg analyte/mL dissolved in the mobile phase, and UV detection at 210/254 nm showed complete inversion and esterification with 0.6% (R)-(+)-10-butyroyloxy-10,11-dihydro-5H-dibenz/b,f/azepine-5-carboxamide with retention time 19.65 minutes and 99.4% (S)-(−)-10-butyroyloxy-10,11-dihydro-5H-dibenz/b,f/azepine-5-carboxamide with retention time of 22.61 minutes.

Example 3

Example 3. (S)-(−)-10-Benzoyloxy-10,11-dihydro-5H-dibenz/b,f/azepine-5-carboxamide To a stirred suspension of (R)-(−)-10,11-dihydro-10-hydroxy-5H-dibenz/b,f/azepine-5-carboxamide (II) (1.0 g, 3.94 mmol) (98.85% optical purity by chiral HPLC analysis), triphenylphosphine (1.03 g, 3.94 mmol) and benzoic acid (0.96 g, 7.88 mmol) in tetrahydrofuran (12 mL) cooled in an ice-water bath was added diisopropylazodicarboxylate (0.80 g, 3.94 mmol) dropwise. After addition was complete, the reaction mixture, which became a yellow solution, was allowed to stir at room temperature for two hours, whereupon the tetrahydrofuran was evaporated (40° C., water-aspirator pressure). Isopropanol (5 mL) was added to the oily residue and the mixture was warmed to the boiling point of the solvent. The mixture was then allowed to cool to room temperature, and then stored at 5° C. for one hour. The precipitate was collected by filtration, and then recrystallised from isopropanol (4 mL). The crystals were collected by filtration and after drying to constant weight, there was obtained (S)-(−)-10-benzoyloxy-10,11-dihydro-5H-dibenz/b,f/azepine-5-carboxamide as white crystals (0.68 g, 48%) of m.p. 167-171° C.

Chiral HPLC analysis of this product (LiChroCART 250-4 HPLC Cartridge ChiraDex 5 μm, (Merck), Flowrate: 0.8 mL/min, Mobile Phase: 0.1M $Na_2HPO_4$ buffer pH7/methanol 88:12, sample injected was 20 μL of 0.2 mg analyte/mL dissolved in the mobile phase, and UV detection at 210/254 nm showed complete inversion and esterification with 21% (R)-(+)-10-benzoyloxy-10,11-dihydro-5H-dibenz/b,f/azepine-5-carboxamide with retention time 42.61 minutes and 78% (S)-(−)-10-benzoyloxy-10,11-dihydro-5H-dibenz/b,f/azepine-5-carboxamide with retention time of 45.4 minutes.

Example 4

Example 4. (S)-(−)-10,11-Dihydro-10-nicotinoyloxy-5H-dibenz/b,f/azepine-5-carboxamide To a stirred suspension of (R)-(−)-10,11-dihydro-10-hydroxy-5H-dibenz/b,f/azepine-5-carboxamide (II) (1.0 g, 3.94 mmol) (98.85% optical purity by chiral HPLC analysis), triphenylphosphine (1.03 g, 3.94 mmol) and nicotinic acid (0.97 g, 7.88 mmol) in tetrahydrofuran (12 mL) cooled in an ice-water bath was added diisopropylazodicarboxylate (0.80 g, 3.94 mmol) dropwise. After addition was complete, the reaction mixture, which became a yellow solution, was allowed to stir at room temperature for two hours, whereupon the tetrahydrofuran was evaporated (40° C., water-aspirator pressure). Isopropanol (5 mL) was added to the oily residue and the mixture was warmed to the boiling point of the solvent. The mixture was then allowed to cool to room temperature, and then stored at 5° C. for one hour. The precipitate was collected by filtration, and then recrystallised from isopropanol (4 mL). The crystals were collected by filtration and after drying to constant weight, there was obtained 10,11-dihydro-10-nicotinoyloxy-5H-dibenz/b,f/azepine-5-carboxamide as white crystals (0.47 g, 34%) of m.p. 167-170° C.

Chiral HPLC analysis of this product (LiChroCART 250-4 HPLC Cartridge ChiraDex 5 μm, (Merck), Flowrate: 0.8 mL/min, Mobile Phase: 0.1M $Na_2HPO_4$ buffer pH7/methanol 88:12, sample injected was 20 μL of 0.2 mg analyte/mL dissolved in the mobile phase, and UV detection at 210/254 nm showed complete inversion and esterification with 21% (R)-(+)-10,11-dihydro-10-nicotinoyloxy-5H-dibenz/b,f/azepine-5-carboxamide with retention time of 22.31 minutes and 75% (S)-(−)-10,11-dihydro-10-nicotinoyloxy-5H-dibenz/b,f/azepine-5-carboxamide with retention time of 28.4 minutes.

Example 5

Example 5. (R)-(+)-10-Acetoxy-10,11-dihydro-5H-dibenz/b,f/azepine-5-carboxamide (VI)

To a stirred suspension of (S)-(+)-10,11-dihydro-10-hydroxy-5H-dibenz/b,f/azepine-5-carboxamide (II) (1.0 g, 3.94 mmol) (99.4% optical purity by chiral HPLC analysis), triphenylphosphine (1.03 g, 3.94 mmol) and acetic acid (0.47 g, 7.88 mmol) in tetrahydrofuran (12 mL) cooled in an ice-water bath was added diisopropylazodicarboxylate (0.80 g, 3.94 mmol) dropwise. After addition was complete, the reaction mixture, which became a cloudy yellow solution was allowed to stir at room temperature for four hours, whereupon the tetrahydrofuran was evaporated (40° C., water-aspirator pressure). Isopropanol (5 mL) was added to the oily residue and the mixture was warmed to the boiling point of the solvent. The mixture was then allowed to cool to room temperature, and then stored at 5° C. for one hour. The precipitate was collected by filtration, and then recrystallised from isopropanol (4 mL). The crystals were collected by filtration and after drying to constant weight, there was obtained (R)-(+)-10-acetoxy-10,11-dihydro-5H-dibenz/b,f/azepine-5-carboxamide (V) as white crystals (0.47 g, 40%) of m.p. 186-187° C.

Chiral HPLC analysis of this product (LiChroCART 250-4 HPLC Cartridge ChiraDex 5 μm, (Merck), Flowrate: 0.8 mL/min, Mobile Phase: 0.1M $Na_2HPO_4$ buffer pH7/methanol 88:12, sample injected was 20 μL of 0.2 mg analyte/mL dissolved in the mobile phase, and UV detection at 210/254 nm showed complete inversion and O-acetylation with 99.5% (R)-(+)-10-acetoxy-10,11-dihydro-5H-dibenz/b,f/azepine-5-carboxamide (VI) with retention time 15.98 minutes and 0.5% (S)-(−)-10-acetoxy-10,11-dihydro-5H-dibenz/b,f/azepine-5-carboxamide (V) with retention time of 21.33 minutes.

In this specification, the expression "optically pure" is used to include compositions which have optical purity of at least 80%, preferably at least 90%, most preferably at least 95%. The upper limit on optical purity may be, for example, 100% or 99.5% or 99%. The expression "optically enriched" means that there is more of one stereoisomer than there is of another stereoisomer in the composition, and, in particular, preferably means that there is at least at least 1% more of one stereoisomer (the "optically enriched" stereoisomer) than there is of the other stereoisomer, i.e., that there is at least 50.5% of the "optically enriched" stereoisomer and up to 49.5% of the other stereoisomer.

It will be appreciated that the invention described above may be modified.

The invention claimed is:

1. A method for the chiral inversion and esterification of optically pure or optically enriched (R)-(−)-10,11-dihydro-10-hydroxy-5H-dibenz/b,f/azepine-5-carboxamide (II) comprising reacting optically pure or optically enriched (R)-(−)-10,11-dihydro-10-hydroxy-5H-dibenz/b,f/azepine-5-carboxamide (II) with a carboxylic acid nucleophile in the presence of a trisubstituted phosphine and a disubstituted azodicarboxylate in a substantially inert solvent.

2. A method for the chiral inversion and esterification of optically pure or optically enriched (S)-(+)-10,11-dihydro-10-hydroxy-5H-dibenz/b,f/azepine-5-carboxamide (I) comprising reacting optically pure or optically enriched (S)-(+)-10,11-dihydro-10-hydroxy-5H-dibenz/b,f/azepine-5-carboxamide (I) with a carboxylic acid nucleophile in the presence of a trisubstituted phosphine and a disubstituted azodicarboxylate in a substantially inert solvent.

3. The method according to claim 1 wherein the carboxylic acid nucleophile is an aliphatic carboxylic acid, straight or branched, containing from one to eighteen carbon atoms, optionally substituted by an aryl group or halogen wherein the term halogen means fluorine, chlorine, bromine or iodine.

4. The method according to claim 1 wherein the carboxylic acid nucleophile is acetic acid.

5. The method according to claim 1 wherein the carboxylic acid nucleophile is an cyclic acid containing from four to seven carbon atoms.

6. The method according to claim 1 wherein the carboxylic acid nucleophile is benzoic acid, optionally substituted by alkoxy, halogen or nitro groups.

7. The method according to claim 1 wherein the carboxylic acid nucleophile is a heteroaromatic acid containing at least one atom of nitrogen.

8. The method according to claim 1 wherein the tri-substituted phosphine is chosen from tri-n-propylphosphine, tri-n-butylphosphine, triphenylphosphine, tri-o-tolylphosphine, diphenyl(2-pyridyl)phosphine, (4-dimethylamino)diphenylphosphine and tris(dimethylamino)phosphine.

9. The method according to claim 1 wherein the disubstituted azodicarboxylate is chosen from dimethylazodicarboxylate, diethyl azodicarboxylate, diisopropylazodicarboxylate, di-tert-butylazodicarboxylate and 1,1'-(azodicarbonyl)dipiperidine.

10. The method according to claim 1 wherein the substantially inert solvent is chosen from dichloromethane, chloroform, carbon tetrachloride, tetrahydrofuran, diethyl ether, dimethylformamide, dioxane and toluene.

11. The method for the preparation of a compound of formula (VIII):

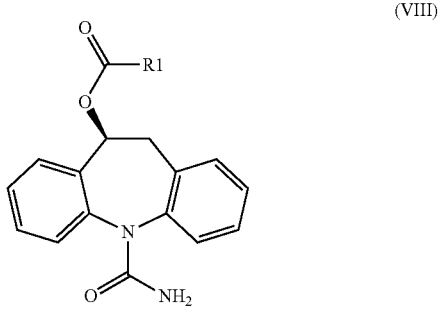

where R1 is hydrogen, alkyl, halogenalkyl, aralkyl, cycloalkyl, cycloalkylalkyl, aryl or pyridyl; the term alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group, said method comprising reacting (R)-(−)-10,11-dihydro-10-hydroxy-5H-dibenz/b,f/azepine-5-carboxamide (II) by a method according to claim 1.

12. The method according to claim 11, wherein the term alkyl means a straight or branched hydrocarbon chain containing from 1 to 8 carbon atoms.

13. The method according to claim 11, wherein the term alkyl means a straight or branched hydrocarbon chain containing from 1 to 4 carbon atoms.

14. The method according to claim 11 wherein the term cycloalkyl means an alicyclic saturated group with 5 or 6 carbon atoms.

15. The method for the preparation of a compound of formula (IX):

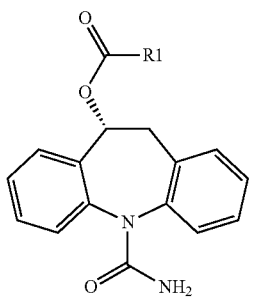

(IX)

where R1 is hydrogen, alkyl, halogenalkyl, aralkyl, cycloalkyl, cycloalkylalkyl, aryl or pyridyl; the term alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group, said method comprising reacting (S)-(+)-10,11-dihydro-10-hydroxy-5H-dibenz/b,f/azepine-5-carboxamide (I) by a method according to claim 2.

16. The method according to claim 15, wherein the term alkyl means a straight or branched hydrocarbon chain containing from 1 to 8 carbon atoms.

17. The method according to claim 15, wherein the term alkyl means a straight or branched hydrocarbon chain containing from 1 to 4 carbon atoms.

18. The method according to claim 15 wherein the term cycloalkyl means an alicyclic saturated group with 5 or 6 carbon atoms.

19. The method for the preparation of (S)-(−)-10-acetoxy-10,11-dihydro-5H-dibenz/b,f/azepine-5-carboxamide (V) comprising reacting optically pure or optically enriched (R)-(−)-10,11-dihydro-10-hydroxy-5H-dibenz/b,f/azepine-5-carboxamide (II) by a method according to claim 1.

20. The method for the preparation of (R)-(+)-10-acetoxy-10,11-dihydro-5H-dibenz/b,f/azepine-5-carboxamide (VI) comprising reacting optically pure or optically enriched (S)-(+)-10,11-dihydro-10-hydroxy-5H-dibenz/b,f/azepine-5-carboxamide (I) by a method according to claim 2.

21. The method according to claim 2 wherein the carboxylic acid nucleophile is an aliphatic carboxylic acid, straight or branched, containing from one to eighteen carbon atoms, optionally substituted by an aryl group or halogen wherein the term halogen means fluorine, chlorine, bromine or iodine.

22. The method according to claim 2 wherein the carboxylic acid nucleophile is acetic acid.

23. The method according to claim 2 wherein the carboxylic acid nucleophile is an cyclic acid containing from four to seven carbon atoms.

24. The method according to claim 2 wherein the carboxylic acid nucleophile is benzoic acid, optionally substituted by alkoxy, halogen or nitro groups.

25. The method according to claim 2 wherein the carboxylic acid nucleophile is a heteroaromatic acid containing at least one atom of nitrogen.

26. The method according to claim 2 wherein the tri-substituted phosphine is chosen from tri-n-propylphosphine, tri-n-butylphosphine, triphenylphosphine, tri-o-tolylphosphine, diphenyl(2-pyridyl)phosphine, (4-dimethylamino)diphenylphosphine and tris(dimethylamino)phosphine.

27. The method according to claim 2 wherein the disubstituted azodicarboxylate is chosen from dimethylazodicarboxylate, diethylazodicarboxylate, diisopropylazodicarboxylate, di-tert-butylazodicarboxylate and 1,1'-(azodicarbonyl)dipiperidine.

28. The method according to claim 2 wherein the substantially inert solvent is chosen from dichloromethane, chloroform, carbon tetrachloride, tetrahydrofuran, diethyl ether, dimethylformamide, dioxane and toluene.

* * * * *